United States Patent
Medasani et al.

(10) Patent No.: US 9,433,656 B2
(45) Date of Patent: Sep. 6, 2016

(54) *PICRORHIZA KURROA* EXTRACT FOR PREVENTION, ELIMINATION AND TREATMENT OF DNA BASED VIRUSES IN HUMANS AND IN BIOTECH INDUSTRY

(75) Inventors: Munisekhar Medasani, Hyderabad (IN); Satyasayee Babu Divi, Vishakapatnam (IN)

(73) Assignee: Munisekhar Medasani, Hyderabad (IN)

( * ) Notice: Subject to any disclaimer, the term of this patent is extended or adjusted under 35 U.S.C. 154(b) by 1158 days.

(21) Appl. No.: 13/390,008

(22) PCT Filed: Aug. 11, 2010

(86) PCT No.: PCT/IN2010/000534
§ 371 (c)(1),
(2), (4) Date: Apr. 27, 2012

(87) PCT Pub. No.: WO2011/024196
PCT Pub. Date: Mar. 3, 2011

(65) Prior Publication Data
US 2012/0219648 A1    Aug. 30, 2012

(30) Foreign Application Priority Data
Aug. 12, 2009   (IN) .......................... 1917/CHE/2009
Sep. 4, 2009    (IN) .......................... 2150/CHE/2009

(51) Int. Cl.
*A01N 65/00*   (2009.01)
*A61K 36/68*   (2006.01)

(52) U.S. Cl.
CPC ................... *A61K 36/68* (2013.01)

(58) Field of Classification Search
CPC ....................................... A61K 36/00

USPC ........................................... 424/725
See application file for complete search history.

(56) References Cited

U.S. PATENT DOCUMENTS

| 2003/0091658 A1 | 5/2003 | Wu |
| 2003/0147969 A1 | 8/2003 | Wu |
| 2006/0246161 A1 | 11/2006 | Xing et al. |
| 2008/0207578 A1 | 8/2008 | Chu et al. |
| 2009/0068291 A1 | 3/2009 | Cyr |

OTHER PUBLICATIONS

Zhang, Y et al. Life Sciences 77 (2005) 3222-323; Cyclooxygenase-2 enzyme inhibitory triterpenoids from Picrorhiza kurroa seeds0.*
Miyazawa et al, Volatile components from the roots of Scrophularia ningpoensis Hemsl. Flavour and Fragrance Journal (2003) vol. 18, No. 5, pp. 398-400.*
Cowan, "Plant Products as Antimicrobial Agents," *Clinical Microbiology Reviews*, 1999, pp. 564-582, vol. 12, No. 4, American Society for Microbiology.
Apr. 26, 2011 Written Opinion issued in International Patent Application No. PCT/IN 10/00534.
Apr. 26, 2011 International Search Report issued in International Patent Application No. PCT/IN 10/00534.

* cited by examiner

*Primary Examiner* — Michael Meller
(74) *Attorney, Agent, or Firm* — Oliff PLC

(57) ABSTRACT

Extract of *picrorhiza kurroa* plants and a process for making the same. The extract has strong anti-viral action against both DNA and RNA-based viruses, and also against bacterial, fungal and protozoan microorganisms. The extract essentially contains the lipophilic compounds occurring in the scrophulariaceae family of plants, in particular, the terpenes and fatty acids thereof. The extract may additionally contain other said lipophilic compounds and the aglycons of the glycosides occurring in said family of plants.

2 Claims, No Drawings

PICRORHIZA KURROA EXTRACT FOR PREVENTION, ELIMINATION AND TREATMENT OF DNA BASED VIRUSES IN HUMANS AND IN BIOTECH INDUSTRY

This invention relates to plant extracts for the treatment of disorders and diseases of the liver and others, and more particularly to the extract, and fractions thereof, of the plant matter of the Scrophulariaceae family of plants for use as medicinal, nutraceutical and food compositions in the prevention, elimination, treatment and management of various liver disorders and diseases arising from viruses and other pathogens and toxic substances; of infections and diseases caused by DNA and RNA-based viruses in general; of infections and diseases/disorders associated with various virus, fungi, bacteria and protozoa; of viral infections to cultures encountered in biotech and fermentation industry; as a hepatoprotective agent; as a prophylactic with regard to liver and other organs and systems and for other applications in the health and care of human and animal subjects and in research and industry. This invention also relates to a process of making said extracts.

The plants of the order Scrophulariaceae are known to possess medicinal properties as reported in traditional medicine systems. The medicinal efficacy of these plants arises from the numerous glycosides present in the plants of this order. The more accessible of Scrophulariaceae plants are the plants in the genus *Picrorhiza*. Three members of this genus are of particular interest because of their safety and absence of toxicity. They are *Picrorhiza kurrooa* Royle, *Picrorhiza scrophulariflora* Pennell and *Neopicrorhiza scrophulariiflora*.

*Picrorhiza kurrooa* (known as Katuka in India) is widely found in India. It grows in the Himalayas at an altitude of about 3000 to 5000 meters. The extract is known for its properties as a liver protector and an immune modulator. Roots of the plant have been traditionally used in the Indian Ayurvedic system of medicine for asthma, bronchitis, malaria, chronic dysentery, viral hepatitis, upset stomach, scorpion stings, as a bitter tonic for stimulating the appetite and for improving digestion. It is known for its therapeutic value as a hepato-protectant and for relief in fevers but there is no disclosure or evidence in the prior art as to whether it acts against hepatitis or other viruses or is a mere rejuvenant of the liver.

The plant also grows in China, Nepal, Bhutan and other regions, where roots and rhizomes thereof have been traditionally used for dysentery, jaundice, steaming of bone, hepatoprotection and immuno-modulation function. The plant, particularly the roots, are known to be rich in terpenoids and glycosides.

The terms *Picrorhiza* and *Picrorrhiza*, with slightly different spellings are interchangeably used in this specification and are intended to be the same material. The species name *Picrorhiza kurrooa* is referred to hereinafter as PK for short in the interests of conciseness. For the purposes of this specification, the initials 'PK' may refer to one of the above mentioned three *Picrorhiza* species or the other or one or more simultaneously. For example, where a mixture of extracts of the said species is being considered, the term PK would refer to all. The meaning appropriate to the context may be taken. The initial 'P' is used as an abbreviation for the term *Picrorhiza*. The terms 'principles' and 'factors' are also used interchangeably in this specification and are intended to mean the same unless otherwise required by the context.

References to 'extraction' in this specification may be to the process of extraction of the plant matter as a whole or to the individual operation of extraction which is one of the steps (the leaching or solid-liquid extraction step) in the said process. The meaning appropriate to the context may be taken. The terms 'component' and 'constituent' have been used interchangeably at some points herein, the meaning being quite clear from the context.

Plant matter refers to the starting material for the process of extraction of the invention the final product appearing at the end thereof being referred to as the extract. The term 'plant matter' has also been used to refer to the plant-matter-in-process that is, at different stages in the process. The liquid streams at various stages in the process are referred to either as the extracts or as the solution. The meaning appropriate to the context may be taken.

The active principle in PK is referred to in the prior art as kutkin which comprises kutkoside which is a glycoside. It further comprises iridoid glycosides named Picroside I, II, III and other picrosides. Several other principles have been identified such as apocynin, drosin and nine cucurbitacin glycosides, the first-named being a potent anti-inflammatory agent and the other two are also reported to have medicinal properties. These medicinal factors occur uniformly across the entire said order (the Scrophulariaceae family) and in particular in all the plants of the P. genus. Thus far, the said medicinal efficacy of PK extracts, has not been attributed to specific active principles (factors) in the prior art.

It is now known that plant matter of the P. genus in particular and the Scrophulariaceae family (S. family for short) in general comprise both lipophilic and non-lipophilic constituents. The lipophilic compounds and constituents of said family are referred to further herein as LCs for short and similarly the non-lipophilic constituents and compounds of the family as the NLCs. This is in the interests of conciseness and without any limitation to the scope of the invention.

These inventors observe that all the above named medicinal factors of PK that have been reported, discussed or investigated either in the traditional medicine practices or in the modern prior art are mainly NLCs. It may be noted that prior art (including traditional medicine practices) has confined itself to use of only water and alcohols (methanol and ethanol) as extracting solvents. These inventors note that said solvents generally speaking, extract the said NLCs, and almost leave out all the LCs. Consequently, the attention of the prior art has been solely on the NLCs and their medicinal properties and has not extended to these other components.

The chief NLC in P. plant matter are the glycosides thereof. In modern times, a wide range of medicinal properties of the various plant glycosides have come to light. They extend over a wide range of diseases and disorders. Different types of glycosides are found in the plant world. The focus and spotlight in the prior art, at least as far as medicinal properties and effects are concerned, has been totally on the P. glycosides. Prior art appears to be unaware of the nature and extent of the other constituents in the S. family of plants, namely the said LCs and their medicinal significance. This is understandable as the prior art has substantially excluded other solvents from their studies, solvents that would have extracted also the LCs to a greater or lesser extent and exposed them to research, study and medicinal scrutiny. Presumably, prior art would then have explored the nature and extent of their medicinal efficacies. Perhaps because the water and alcohol extracts exhibited considerable medicinal efficacy and offered enough scope for investigations, attention did not extend to the other extracting solvents and thereby to the lipophilic constituents of the S. family.

Through their experimental observations, these inventors have established that the medicinal activity of said LCs (lipophilic compounds of the S. family) is of a very high order. It would not be incorrect to say that the range and quantum of the medicinal effect of the said NLCs in contrast to said glycosides is considerably and surprisingly higher and wider. This invention is the first to consider the said LCs and to verify their quite extraordinary medical significance, for example, as anti-viral compounds. This invention has also established for the first time that the presence of NLCs tends to impair and reduce the medicinal efficacy of the LCs and that it is therefore important to produce PK extracts that contain the LCs substantially exclusively or with the minimum of NLC content. To this end, these inventors provide a novel process and have identified appropriate solvents that preferentially extract said LCs and whose extraction profile is such as to substantially keep out said NLCs.

These inventors observe that the NLCs mask the medicinal effects of the LCs. The presence of any NLCs in an extract containing the said LCs has the effect of reducing the medicinal efficacy of the latter. It may be that some of the NLCs of the S. family have an action opposite to that of the LCs. Whatever the mechanism, this invention has experimentally established that the LCs have pronounced medicinal effects and that LC-extracts must be preferably substantially free of NLCs so as to realise their full medicinal efficacy.

The novel PK extract of the invention therefore differs in a very fundamental way from the PK extracts of prior art in that the medicinal principles in the former are different from that in the latter. The medicinal principles of the former are substantially absent in the latter and the medicinal principles in the latter have been substantially avoided in the former for reasons elaborated hereinbelow. The medicinal principles in the former are the LCs of the S. family of plants and not the S. family glycosides as is the case with the latter.

The chief medicinal factors in the former are the fatty acids and terpenes found in the S. family of plants followed by the aglycons arising from the S. family glycosides. Said fatty acids, terpenes and aglycons evolved in the process are absent in the latter. As is known, the glycosides in PK plants are the picrosides I, II and III etc. The latter therefore consists mainly of said picrosides and a compound named apocynin while the former is substantially free of both said picrosides and other glycosides and also apocynin. Rather than the said picrosides present in the original plant matter, what we have in the extract of the invention are aglycons derived therefrom.

It may therefore be noted that the process of the invention is not merely a physical process of extraction but incorporates chemical changes. These inventors observe that hydrolysis and esterification reactions are occurring during the process of extraction resulting in the release of said aglycons in the extract. This hypothesis is submitted without commitment, as the higher medicinal efficacy has already been established by experimental observation. This invention has experimental proof that chemical reactions are occurring during extraction so that the extraction process of the invention involves a combination of physical and chemical changes. This invention prepared a hexane extract and also an extract wherein the first solvent was ethanol and the second was hexane. The yield in the former procedure was found to be about 35% greater LCs. HPLC analysis indicates the presence of aglycons, steroidal terpenes and long chain fatty acids structures in the extract. It is inferred that the extra yield corresponds to the existence of these aglycons, steroidal terpenes and long chain fatty acids present in the hexane extract. These compounds, which are either originally present in the S family plant matter or are reaction products involving said compounds, are substantially absent in the extract obtained by the ethanol-hexane solvent system. The ethanol-hexane solvent system leaves out these components during extraction.

The extract of the invention further contains the fatty acids found in the S. family plants. The S. family glycosides are highly bitter compounds that make the prior art PK extracts unpalatable. In contrast, the PK extract of the invention is highly palatable being totally free of bitterness factors. A number of odour factors come out in water and alcohol extracts and consequently the prior art PK extracts have a strong unpleasant odour that reduces their acceptability for human and animal consumption. Said picrosides and other glycosides in the S. family are highly bitter compounds. Smaller quantities of other bitter principles are also found in PK plants. On the other hand, the extract of the invention is substantially odourless. All in all, the extract of the invention is a distinct and different paradigm from the prior art extracts.

The mechanism of the medicinal action of the terpenes and other components of the extract of the invention is not known nor is there an explanation of the superiority of their medicinal action vis-à-vis the prior art extract components. But these inventors stress that the said superior medicinal activity is experimentally established by this invention.

The drawbacks of the prior art extracts are therefore, the presence of the glycoside components that are of considerably lesser medicinal efficacy than the said terpenes and other LCs of the S. family of plants. The range of medicinal effectiveness of the glycosides is also considerably lesser than that of the said terpenes and other LCs. Although they are hepatoprotective, the said glycosides do not possess anti-viral activity. The said LCs on the other hand, exhibit strong anti-viral activity both against DNA and RNA viruses and their action is therefore much wider than the limited liver-protective and regenerative action of the said NLCs. The prior art extracts are highly bitter such as to be almost unpalatable and their unacceptability extends further to their strong unpleasant odour components.

The drawbacks of the prior art processes of extraction are that they are confined to water and the two alcohols, ethanol and methanol and do not extend to a whole range of solvents that yield novel and better and more useful extracts containing the LCs of the S. family.

These inventors have experimentally established through cell lines that the use of PK mainly comprising said lipophilic components actively inhibits the action of hepatitic and other viruses of DNA and RNA types. It further destructs the viral structures providing confirmation that it is a highly effective anti-viral composition.

As is known, phospholipids involved the structure of cell membranes comprise two highly lipophilic (fat-loving) alkyl chains and a highly hydrophilic (water-loving) ionic group at the other end, typified by choline phosphate. The inventors believe that this allows the lipophilic moieties in PK extracts to be more active pharmacologically in the treatment of viral diseases. The in vitro investigations by the present inventors have been confirmed by independent labs. They confirm that PK lipophilic compounds have very high anti-viral properties against DNA and RNA viruses including Hepatitis B, influenza, retroviruses such as HIV, and other viruses.

It is therefore the object of this invention to provide a PK extract wherein the lipophilic components of PK plant matter are substantially the major components thereof.

It is a further object of this invention to provide a PK extract wherein substantially all the lipophilic components of PK are faithfully represented in the extract.

It is a further object of the invention to provide a PK extract wherein the non-lipophilic components of PK are substantially absent or are minimised.

It is a still further object of this invention to provide a PK extract wherein the bitter principles, in particular the PK glycosides and the unpleasant odour components present in PK are substantially absent or are minimised.

It is a further object of the invention to provide for a process of extraction for making a PK extract wherein said lipophilic factors are the major components and wherein the non-lipophilic factors of PK are substantially absent or minimised.

It is a still further object of this invention to provide for a said extraction process such that the full set of lipophilic factors originally present in the PK plant matter are faithfully brought out in the extract and that said hydrolysis and esterification reactions are allowed to proceed or indeed encouraged.

It is a further object of this invention to provide a process of extraction for making a PK extract wherein the extraction of the terpenes and the fatty acids in the original plant matter is maximised and further the maximum conversion of the glycosides to aglycons and subsequent extraction thereof is achieved by the suitable selection of solvents and the choice of extraction parameters.

It is a still further object of this invention to provide a set of solvents whereby PK extraction can be carried out to obtain an extract, the major components whereof are said lipophilic compounds and that substantially prevent, or minimise the extracting out of the non-lipophilic constituents and/or the bitter and the unpleasant odour components thereof originally present in the PK plant matter being extracted.

According to the invention, therefore, there is provided an extract, or fractions thereof, of the plant matter of the Scrophulariaceae family of plants, for use as medicinal, nutraceutical and food compositions in the prevention, elimination, treatment and management of various liver disorders and diseases arising from viruses and other pathogens and toxic substances; of infections and diseases caused by DNA and RNA-based viruses in general; of infections and diseases/disorders associated with various virus, fungi, bacteria and protozoa; viral infections to cultures encountered in biotech and fermentation industry; as a hepatoprotective agent; as a prophylactic with regard to liver and other organs and systems and for other applications in the health and care of human and animal subjects and in research and industry, said extract comprising the lipophilic constituents of the said family of plants, the major said lipophilic constituent therein being one or more of the terpenes of said family of plants.

According to the invention, therefore, there is further provided a process of extraction for the plant matter from one or more plants of the Scrophulariaceae family of plants comprising the steps of obtaining the plant matter to be extracted; subjecting the said plant matter to a preparatory operation as required such as cutting, chopping, blanching, drying, crushing, grinding, sieving or others; contacting the plant matter from the preparatory step with a pre-determined non-aqueous solvent, series of solvents, or a solvent mixture, that preferentially extracts the lipophilic components in the plant matter at pre-determined temperature and for a pre-determined duration of time in one or more extraction operations arranged in series, or parallel or a hybrid configuration, separation of the extract solution from the plant matter in process by any of the known means; separating the solvent from the extract solution by any of the known means such as evaporation of the solvent to yield either a concentrated extract solution or a solid form product.

The PK extract of the invention therefore essentially comprises the terpene constituents of the S. family of plants. The extract may comprise one said terpene or any mixture of the terpenes of the S. family. Preferably, the terpenes are the single major components in the extract and the terpenes and fatty acids are the major part of the said lipophilic components in the extract. The extract further comprises the fatty acids of the S. family of plants. The PK extract of the invention also essentially comprises the aglycons of the glycosides present in the S. family plants. These glycosides undergo reactions (like hydrolysis) or decomposition under the extraction conditions and yield their respective aglycons that are then extracted out by the solvents of the invention into the extract. Preferably, the combined amount of the said terpenes, fatty acids and the aglycons, that is of the LCs as a whole is 80% by wt or more. Preferably, the extract of the invention is free of the said bitter glycosides and the amount of the other NLCs in the extract is between 0.01% by wt. and 20% by wt of the extract as a whole. Preferably, the amount of said glycosides, kutkisides, picrosides and apocynin and drosin together does not exceed 20% by wt of the extract. Preferably less than 10% of the extract is water-soluble.

Within the scope of the invention, the said PK extract of the invention may be the extract of any species in said S. family of plants. It will be noted that the process of extraction of the invention is easily and simply extensible to any said species. Equally easily and simply the said process is adaptable to any mixture of said species. Preferably, the extract is from a mixture of the three species mentioned hereinabove: *Picrorhiza kurrooa* Royle, *Picrorhiza scrophulariflora* Pennell and *Neopicrorhiza scrophulariiflora*. These three species are favoured from the point of view of toxicity.

The plant matter used for extraction may be any part of the plant such as the roots, rhizomes, stem, leaves, flowers, bark, seeds and others. Within the scope of the invention, any mixture or combination of said parts may be extracted. Preferably, the plant matter extracted is either the roots or the rhizomes, more preferably a mixture of the two. Any other mixture of said parts is also within the scope of the invention.

The extraction process of the invention is a solid-liquid extraction process. As mentioned hereinabove, the plant matter may be any plant of the S. family of plants. Within the scope of the invention, it can be a mixture of plant matter from different said plants. Preferably, the plant matter is from the species *Picrorhiza kurrooa* Royle or from *Picrorhiza scrophulariflora* Pennell or *Neopicrorhiza scrophulariiflora* or any mixture or combination of the three species.

The said preparatory steps are optional and one or more thereof may be adopted as required. Extraction can be carried out on wet or dry plant matter. Preferably, the matter is pre-dried either by solar drying or process drying. Preferably the plant matter is cut and chopped to reduce the size to ensure better solid-liquid contact in the extraction step. Preferably, the plant matter is crushed and ground to a size range of about 1-5 mm size or below. Preferably a blanching operation is carried out.

The solvent adopted in the process of the invention is non-aqueous. It is preferably non-polar, but polar and other solvents are within the scope of the invention. Preferably it is non-alcoholic but monohydric alcohols of chain length of four or more C-atoms may be used even though they are polar. The solvent preferably either has a hydrocarbon chain of four or more C-atoms in its structure or a cyclic or ring portion therein. Without limitation to the scope of the invention the solvent may be one from the following list:

Dichloromethane, hexane, n-hexane, c-hexane, toluene, t-BuOMe, Et2O, Methyl Iso Butyl Ketone, Vinylacetate, ethyl acetate, t-butanol, DMA, i-propanol, formic acid, formamide, methyl ethyl ketone, N,N-dimethylformamide, acetic acid, acetone, acetonitrile, benzene, 1-butanol, 2-butanol, 2-butanone, 1-butyl alcohol, carbon tetrachloride, chlorobenzene, chloroform, cyclohexame, 1,2-dichloroethane, diethyl ether, diethylene glycol, diglyme (diethylene glycol dimethyl ether), 1,2-dimethoxy-ethane (glyme, DME), dimethylether, dimethyl-formamide (DMF), dimethyl sulphoxide (DMSO), dioxane, ethanol, ethyl acetate, ethylene glycol, glycerine, heptane, hexamethylphosphoramide (HMPA), hexamethylphosphorous triamide (HMPT), methanol, methyl t-butyl ether (MTBE), methylene chloride, N-methyl-2-pyrrolidinone (NMP), nitromethane, pentane, petroleum ether (ligroine), 1-propanol, 2-propanol, pyridine, tetrahydrofuran (THF), triethyl amine, o-, m- and p-xylenes, white spirit, vegetable oils, petroleum naphtha, turpentine, oxygenated solvents (like alcohols, glycol ethers, methyl acetate, ethyl acetate, ketones, esters, glycol ether, glycol esters); organic compounds used as solvents include aromatic compounds and other hydrocarbons, alcohols, esters, ethers, ketones, amines, and nitrated and halogenated hydrocarbons, inorganic solvents like ammonia, sulphuric acid, sulphuryl chloride fluoride, surfactants, detergents, pH buffers, water and heavy water.

Within the scope of the invention the extraction may be carried out with a solvent mixture of any two or more of the above solvents. Alternatively, within the scope of the invention, extraction may be carried out in series employing two or more solvents selected from the above.

The process of extraction of the invention comprises a solid-liquid extraction step wherein the plant matter is contacted with a suitable solvent(s). The extract of the invention may be produced by the process of the invention or other within the scope of the invention. Within the scope of the invention, the extract of the invention may be prepared by any of the known means for carrying out the extraction step such as: solvent extraction, absorbent gel extraction, liquefied gas (like CO2) extraction, enzymatic process, membrane filtration, liquid-liquid extraction, liquid-solid extraction, resin extraction, reverse phase extraction, chromatography or others.

Within the scope of the invention, the extract product of the invention after removal of the solvent by evaporation or other means may be dried or subjected to other operations such as grinding, screening, adsorbing on excipients or others. The extract may be in the form of nanoparticles, nano gels or processed to constitute a vaccine or an adjuvant.

Within the scope of the invention, the extract of the invention may further contain one or more of the following constituents of the said S. family of plants: glycoside esters, glycoside ethers, aliphatic compounds, aromatic compounds, glycosidic carboxylates, steroidal glycosides, long chain fatty acids, aglycones, acylated aglycons, fatty alcohols, fatty acids, steroidal esters, steroidal fatty acids, steroidal alcohols, sterols, terpenoids, steroidal triterpenes, oxidised triterpenes, esters of triterpenes, acids of triterpenes, alcohols of triterpenes, cucurbitacins, terpenoid moieties having 5-40 C-atoms, long-chain hydroxyl fatty acid moieties, resin acids, triterpenoids built on steroidal skeleton.

Within the scope of the invention, the extract may be in any of the known forms for administration orally, intravenously, intramuscularly, subcutaneously, peritoneally, rectally, nasally trans-dermally, dermally, sublingually or others. It may also be in the form of any of the known medicinal salts and may comprise additives for colour, flavour, taste, texture and others. The extract of the invention may also contain additional therapeutic factors as added additives that provide either additional efficacy or combination therapeutic effect or both. Said additives may be nutrition factors to yield a nutraceutical or food composition with therapeutic action. Examples of such additives are: sugars, vitamins, minerals, amino acids, metals, oils, fatty acids, alcohols, solvents and other plant extracts. The extract of the invention may be a solid form composition or a solution of said lipophilic components in a suitable base or adsorbed on any of the known excipients. The extract of the invention may be optionally processed further to modify its properties, form, shape, colour, texture and it increase its effectiveness and acceptability. Any such modified forms of the said extract are within the scope of the invention. Examples of such modifying processes are: Standardization of extract, fractionation to obtain different fractions, homogenization, fortification and others.

The extract of the invention may be in the form of a fraction within the scope of the invention. The extract may be fractionated by any of the known means such as HPLC—High Performance Liquid Chromatography, Gas Chromatography (GC) or others. Within the scope of the invention, any of said fractions or mixtures thereof may constitute the extract of the invention.

Preferably, it is a non-polar hydrocarbon solvent. More preferably, the solvent is n-hexane.

In order to provide a clearer understanding of the invention some of the embodiments thereof are described hereinbelow without limitation to the scope of the invention.

EMBODIMENT 1

1. Roots and rhizomes of said PK plants were procured and sun-dried. Manual picking of foreign particles was carried out.
2. The plant matter was subjected to water washing by means of sprinklers to remove sand and dirt.
3. The plant matter was then air dried under vacuum to bring down the moisture.
4. The plant matter was then ground manually and the ground matter air dried to remove traces of moisture.
5. A batch of this matter was weighed and charged into the reactor (extraction vessel).
6. Hexane was added and the solid-liquid mixture heated. (Alternative any other non-polar solvent).
7. The heated mixture was continuously stirred.
8. The extraction process including the said reactions were allowed to proceed for a period of about 24 hours.
9. The plant matter and the solution were separated.
10. The solution was transferred to another vessel under vacuum.
11. The solution was filtered thrice to remove suspended matter and undissolved matter and thereafter the solution was sent to a reaction vessel (evaporator) where the solvent was evaporated under vacuum. The temperature was maintained at below 70 C during evaporation.

12. The solvent was recovered and sent for re-use in the extraction.
13. The solid residue resulting from evaporation was air dried under vacuum in a controlled atmosphere. The dried material is the extract product of the invention and the same was sent for testing.

EMBODIMENT 2

1. Steps 1 and 2 as in embodiment 1.
2. The PK plant matter was ground into small pieces by mechanical means.
3. A batch was measured out and loaded into the reactor (extraction vessel).
4. A mixture of solvents, pentane and ethyl acetate was charged to the reactor. (Alternatives: Any mixture of pentane, ethyl acetate, acetone, n-hexane, ether, chloroform and tetrahydrofuran).
5. Reactor contents heated and stirred continuously. Extraction carried out for about 36 hours.
6. Separation of the plant matter and solution carried out.
7. The solution was transferred to another vessel under vacuum.
8. The solution was filtered thrice and the clear liquid was evaporated at about 80 C under vacuum.
9. Solvent recovered.
10. The solid residue from the evaporation collected and subjected to air drying under vacuum in an atmosphere of nitrogen (alternatively carbon dioxide).
11. The dried product is the product extract of the invention. It was sent for testing.

EMBODIMENT 3

1. Same steps as 1 and 2 of embodiment 1.
2. The PK plant matter was mashed into a paste and mixed with sufficient quantity of water.
3. Organic acid (alternatively an inorganic acid) was added to bring down the pH so as to initiate the esterification reaction of the glycosides.
4. Stirring continued for about 24 hours.
5. At this stage, the n-hexane solvent was added (alternatively petroleum ether) and extraction continued for about 4 hours with stirring.
6. The solution was decanted and filtered.
7. The solvent was evaporated from the solution under vacuum by heating at about 75 C.
8. The semi-solid residue was collected and lypolised at about 80 C under vacuum and further process to obtain it in a powdered form.
9. The powder is the extract product of the invention and was sent for testing.

EMBODIMENT 4

1. Same as steps 1 and 2 of embodiment 1.
2. The PK plant matter is ground into a paste and steam distilled.
3. The steam is condensed and the residual solution after steam distillation is collected.
4. Enzyme esterase is added. pH and temperature are adjusted and the solution stirred for about 6 hours.
5. The temperature was raised to about 100 C to under vacuum to denature the enzyme.
6. The solution was then cooled.
7. Petroleum ether was added and the mixture stirred for about 4 hours.
8. The solution was filtered to remove the enzyme debris and un-dissolved particles.
9. The solution was separated into a petroleum ether layer and an aqueous layer.
10. The petroleum ether was heated to evaporate the solvent under vacuum.
11. The solid residue was collected being the extract product of the invention.
12. The extract product was air dried and sent for testing.
13. The water was evaporated from the aqueous layer. The evaporation was under vacuum. The residue contains the water soluble components in the PK plant matter.

EMBODIMENT 5

1. Same as steps 1, 2 and 3 of embodiment 1.
2. The PK plant matter is ground into small pieces by mechanical means.
3. A batch is measured out and loaded into the extractor reactor.
4. A measured quantity of solvent ethanol (alternative: methanol) charged to the reactor.
5. Reactor contents heated to the required level while stirring and maintained at those conditions for about 24 hours.
6. The solution is transferred to another reactor vessel under vacuum.
7. The solution was filtered three times.
8. Water is added to the solution and stirred for about 1 hour.
9. Solvent n-hexane (alternatively pentane) added and the contents stirred for about 6 hours.
10. The solution is allowed to settle for about 4 hours.
11. Evaporation under vacuum carried out to distill off the solvent to recover the extract product of the invention in a solid or semi-solid form.
12. Balance liquid containing water and alcohol is distilled to recover the solvent.
13. Product air dried under vacuum in nitrogen atmosphere (alternatively CO2 atmosphere) and sent for testing and microbial examination.

EMBODIMENT 6

1. Steps 1 to 3 same as in embodiment 1.
2. Same as item 2 in embodiment 5.
3. A batch of the PK plant matter is measured out and loaded into the extractor reactor.
4. The reactor is charged with the required quantity of n-hexane (alternative solvents for this embodiment: pentane, 1,4-di-oxane, di-ethyl ether and petroleum ether.
5. The reactor contents are heated to the required level and stirred for about 24 hours.
6. The solution transferred to another vessel under vacuum and filtered three times.
7. The solution heated to evaporate the solvent under vacuum to obtain the extract product of the invention in solid or semi-solid form.
8. Residual solvent removed from product by air drying under vacuum in a nitrogen atmosphere (alternatively a CO2 atmosphere).
9. Product sent for testing for physical properties and microbial evaluation.

Embodiments and variations other than described herein above are feasible by persons skilled in the art and the same are within the scope and spirit of this invention.

We claim:

1. A medicinal, nutraceutical, or food composition in the form of a tablet or capsule for elimination, treatment, or management of liver disorders, liver diseases, or immuno-modulation in a human in need thereof consisting essentially of a therapeutically effective amount of a hexane and liquid carbon dioxide extract of *Picrorhiza kurroa*.

2. The medicinal, nutraceutical, or food composition in the form of a tablet or capsule as recited in claim 1, wherein the immuno-modulation is for the elimination, treatment and modulation of infections and diseases selected from the group consisting of herpes, hepatitis virus, influenza, oropharyngeal candidiasis, zygomycosis, sporotrichosis, *mycobacterium tuberculosis, streptococcus pneumoniae, enterohemorrahagic E. coli*, malaria parasite, and retroviruses.

* * * * *